United States Patent [19]

Fedotov et al.

[11] Patent Number: 4,629,107
[45] Date of Patent: Dec. 16, 1986

[54] LIGATING INSTRUMENT

[75] Inventors: Vladimir M. Fedotov; Vladimir P. Kharchenko, both of Moscow; Iosif L. Lipovsky, Leningrad; Tatyana L. Ivanova, Moscow, all of U.S.S.R.

[73] Assignee: Vsesojuzny Nauchno-Issledovatelsky I Ispytatelny Institute Meditsinskoi Tekhniki, Moscow, U.S.S.R.

[21] Appl. No.: 617,508

[22] Filed: Jun. 5, 1984

[30] Foreign Application Priority Data

Aug. 19, 1983 [SU] U.S.S.R. ................... 364947

[51] Int. Cl.[4] ............................................. A61B 17/10
[52] U.S. Cl. ................... 227/19; 128/334 R; 227/DIG. 1
[58] Field of Search ................. 128/334 R, 334 C; 227/DIG. 1, 19

[56] References Cited

U.S. PATENT DOCUMENTS 3,079,606  3/1963  Bobrov et al. .................... 1/120
4,143,660  3/1979  Malyshev et al. ............. 128/303.1
4,290,542  9/1981  Fedotov et al. .................... 227/155

Primary Examiner—Michael H. Thaler
Attorney, Agent, or Firm—Fleit, Jacobson, Cohn & Price

[57] ABSTRACT

A ligating instrument comprising an anvil body and a staple driving body with a longitudinal groove which accommodates a staple magazine with staple pushers and a wedge. The latter is mounted on a carriage arranged in guides provided on the lateral walls of the staple driving body. The instrument incorporates a device for adjusting the ligation spacing, which comprises a stationary axle mounted on the carriage transversely to the latter. The tapered portion of the wedge is fitted on this axle. The ligation spacing adjustment means also includes a movable support articulated to the wedge in its rear portion so that the movable support and the wedge can be set in motion at a perpendicular to the guides of the carriage.

2 Claims, 4 Drawing Figures

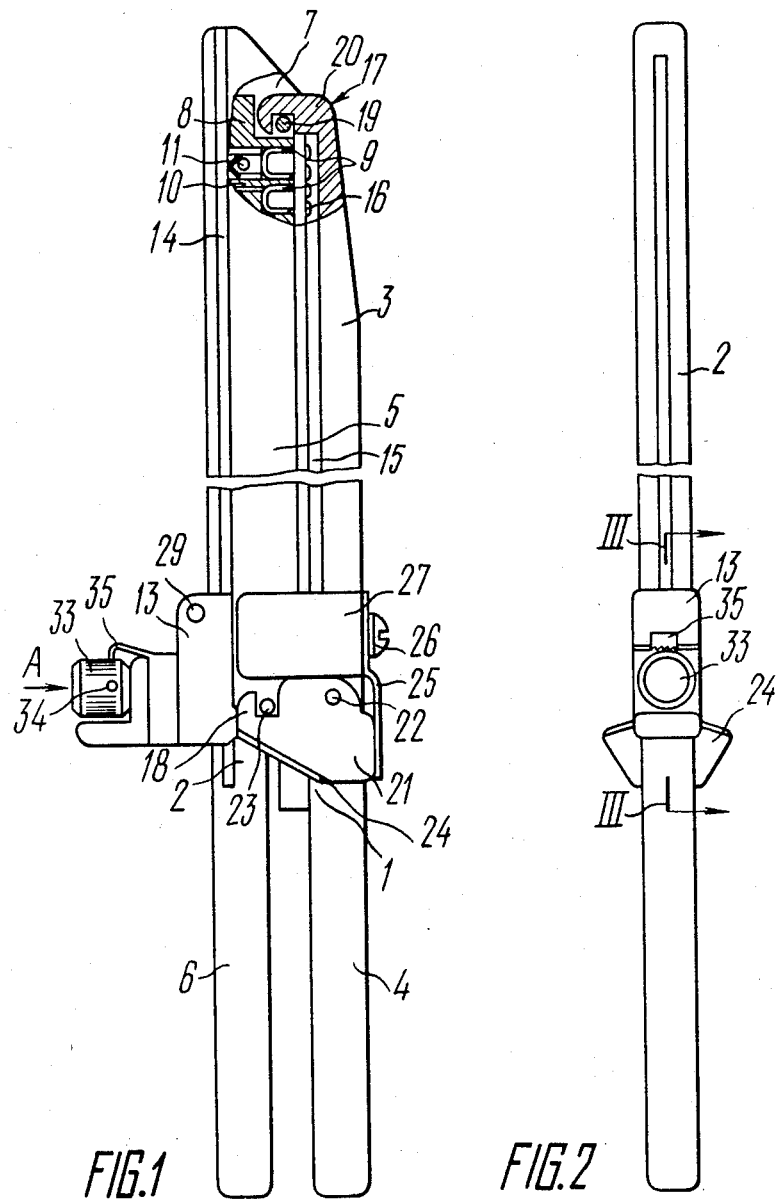

LIGATING INSTRUMENT

FIELD OF THE INVENTION

The present invention relates to medical equipment and is more particularly concerned with a ligating instrument.

The ligating instrument according to the invention is best applicable to ligating organs of the gastrointestinal tract.

It can also be used for ligating the esophagus, lungs, vessels and other organs of man and animals.

BACKGROUND OF THE INVENTION

Ligation of tissues and organs is an essential stage of a surgical intervention, which largely determines the result and the very possibility of the operation. The effectiveness of ligation, in turn, depends on the ligating instrument, which must be such as to provide aerostatic and hemostatic ligations. A ligating instrument must be capable of adjusting the ligation spacing depending on the thickness of the tissue being ligated over a broad range so as to meet all practical requirements. It must also be as compact as possible so that it can be easily handled in the operative wound.

There is known an instrument for ligating blood vessels with metal staples according to U.S. Pat. No. 3,079,608. It comprises an anvil body and a staple driving body held together by a detachable joint and a locking means. The staple driving body has a working portion with staple channels extending transversely to the longitudinal axis of the staple driving body. The channels accommodate U-shaped staples and staple pushers which serve to push the staples out of the channels during ligating. In pushing out the staples, the staple pushers interact with a tapered wedge movable along the working portion of the staple driving body.

The wedge is mounted on the end of a strip close to the working portion of the staple driving body. The opposite end of the strip is connected to a carriage movably arranged in a recess provided in the staple driving body.

The anvil body has a working portion which is opposite the working portion of the staple driving body during operation. The working portion of the anvil body carries an anvil. As staples are pushed out from the staple channels, they are brought into engagement with the anvil and their ends are bent. In order to bend the ends of the staples, the anvil is provided with two rows of hollows. With the ligating instrument fully assembled, the rows of hollows extend along the entire length of the working portion of the anvil body opposite the staple channels of the staple driving body.

The locking means for holding together the staple driving body and anvil body is a rack-and-pinion means. As the staple driving body and anvil body are brought together or apart, the rack and pinion teeth are successively thrown into engagement and discretely lock the working portions of the staple driving and anvil bodies in relation to each other, thus making it possible to adjust the ligation spacing depending on the thickness of the tissue being ligated.

The ligating instrument in question is disadvantageous in that the ligation spacing can only be adjusted over a very narrow range. The instrument is too long, for its overall length is a sum total of the length of the working portion of the staple driving body, which corresponds to the length of the suture, and the length of the strip carrying the wedge, which is as long as the working portion of the staple driving body.

The design of the ligating instrument in question fails to increase the range of ligation spacings, for increasing that range seriously impairs the quality of the suture along its length. The reason for this lies in that the working portions of the staple driving body and anvil body, which compress the biological tissue, do not move in parallel with each other.

The above disadvantages are partially eliminated in a ligating instrument according to USSR Inventor's Certificate No. 886,897, which comprises an anvil body and a staple driving body. The staple driving body has a working portion with a longitudinal groove formed by its lateral walls. The longitudinal groove accommodates a magazine whose external shape is identical with the shape of the groove. The magazine contains a plurality of U-shaped staples received in sockets uniformly spaced over the entire length of the magazine. The same sockets accommodate staple pushers.

Each staple pusher is shaped as a right-angle prism with a bevelled surface facing the bottom of the magazine. The opposite side of the prism, which faces the staples and comes in contact with them, is flat. The staple driving body is provided with a handle having a ring, which is intended to be grasped by the hand. In pushing out the staples, the staple pushers interact with a tapered wedge which is movable along the working portion of the staple driving body. The wedge is mounted on the end of a strip and is close to the working portion of the staple driving body. The opposite end of the strip is connected to a carriage movably arranged in a groove provided in the staple driving body.

The anvil body has a working portion which is opposite the working portion of the staple driving body when the two bodies are held together. A longitudinal groove is provided over the entire length of the anvil body. This groove is formed by the lateral walls of the working portion of the anvil body. It receives an anvil with hollows. Staples are brought into engagement with the hollows, whereby their ends are bent for ligation.

The ligation spacing is adjusted over a desired range by moving the anvil toward the working portion of the staple driving body by a means for adjusting the ligation spacing, which is accommodated in the working portion of the staple driving body.

The means for adjusting the ligation spacing is a crankshaft with a handle for rotating the crankshaft. The anvil is a right-angle prism. Hollows are provided on the lateral side of the prism, which faces the working portion of the staple driving body and compresses the biological tissue being ligated. The hollows are arranged strictly opposite the sockets of the magazine.

The anvil is provided with a longitudinal recess which receives the crank of the crankshaft. As the crankshaft is rotated by the handle, the anvil moves toward the working portion of the staple driving body, changing the distance between the surfaces of the anvil and the working portion of the staple driving body which compress the biological tissue. In this way the ligation spacing is adjusted.

The anvil body has a handle with a ring. The handle is designed to be grasped by the hand.

The ligating instrument further incorporates a detachable joint and a locking means which serve to hold the anvil body and the staple driving body together. The detachable joint is located at the point where the working portions of the anvil body and staple driving body are joined together. The detachable joint is an axle mounted on the staple driving body and having its end received in a hole provided in the anvil body. The locking means is a two-tooth rack-and-pinion means arranged in proximity to the handle with the ring.

In the latter ligating instrument, the ligation spacing adjustment means is not kinematically coupled to the wedge. This necessitates the use of said strip, which increases the length of the staple driving body and anvil body and the overall length of the instrument, since the latter is a sum total of the length of the working portion of the staple driving body, corresponding to the suture length, and the length of the strip carrying the wedge, which is as long as the working portion of the staple driving body.

The ligating instrument under review is hard to manipulate in an operative wound. It is quite difficult to bring its working members to the suture area in order to ligate a lung between the lobes.

SUMMARY OF THE INVENTION

It is the principal object of the present invention to provide a ligating instrument with a means for adjusting the ligation spacing designed so as to minimize the size of the instrument.

It is another object of the invention to provide a ligating instrument which would be reliable and easy to manipulate in an operative wound.

It is still another object of the invention to provide a ligating instrument of a simple design.

The invention provides a ligating instrument which comprises an anvil body and a staple driving body whose lateral walls form a longitudinal groove receiving a staple magazine containing staples and having staple pushers and a wedge which interacts with the staple pushers in order to push out the staples and is mounted on a carriage arranged in guides extending along the staple driving body, the anvil body having an anvil for bending the ends of the staples as they are brought into engagement with the anvil, as well as a detachable joint and a locking means intended to hold the anvil body and the staple driving body together, and a means for adjusting the ligation spacing, which ligating instrument is characterized, according to the invention, in that the guides of the carriage are provided on the external sides of the lateral walls of the staple driving body, and in that the means for adjusting the ligation spacing has a stationary axle secured across the carriage with the tapered portion of the wedge fitted on said axle, and a movable support articulated to the wedge in its rear portion so that both are enabled to move at a perpendicular to the guides of the carriage.

Mounting the carriage in the guides provided on the external sides of the lateral walls of the staple driving body and the direct connection of the means for adjusting the ligation spacing to the wedge mounted on two supports, i.e., the stationary axle on which the wedge is fitted with its tapered portion, and the movable support at the rear portion of the wedge, would make it possible to reduce the size of the ligating instrument. As a result, it is easy to manipulate the instrument in an operative wound.

It is preferred that the means for adjusting the ligation spacing have a screw received in the body of the carriage transversely to its guides and having a head of a round longitudinal section which serves as the movable support and moves with the wedge under the action of a force applied to a nut screwed on the screw.

The ligating instrument according to the invention makes it possible to adjust the ligation spacing over any desired thickness range and has a small size so that it is easy to manipulate the instrument in an operative wound.

BRIEF DESCRIPTION OF THE ACCOMPANYING DRAWINGS

Other objects and advantages of the present invention will become more apparent from a consideration of the following detailed description of a preferred embodiment thereof, taken in conjunction with the accompanying drawings, wherein:

FIG. 1 is a schematic cut-away side view of a ligating instrument in accordance with the invention;

FIG. 2 is a view in the direction of the arrow A in FIG. 1;

DETAILED DESCRIPTION OF THE INVENTION

Figure 3:
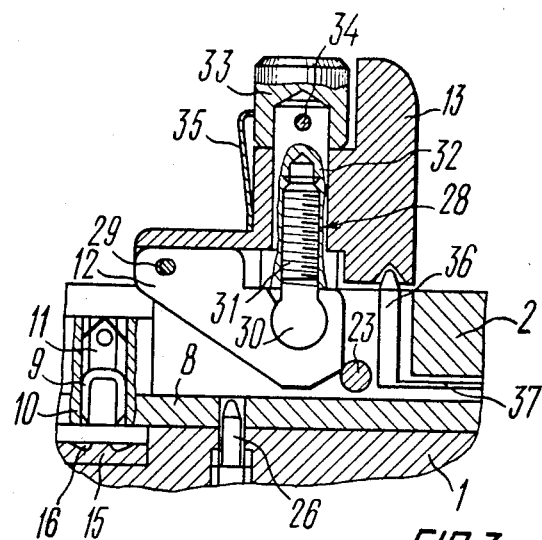
FIG. 3 is a section taken on line III—III in FIG. 2, showing the ligating instrument according to the invention ready for ligation.

With continued reference to the attached drawings, there is shown a ligating instrument comprising an anvil body 1 (FIG. 1) and a staple driving body 2 (FIGS. 1 and 2). The anvil body 1 has a working portion 3 (FIG. 1) and a handle 4. The staple driving body 2 has a working portion 5 and a handle 6. The lateral walls of the staple driving body 2 have no reference numbers. They form a longitudinal groove 7 extending over the entire length of the working portion 5 of the staple driving body 2. The longitudinal groove 7 receives a staple magazine 8 which extends over its entire length. The external shape of the staple magazine 8 is identical with the shape of the groove 7. The magazine 8 contains a plurality of U-shaped staples 9 arranged in two rows (not shown) over the entire length of the magazine 8. The staples 9 are arranged in sockets formed by equidistant partitions 10 of the magazine 8.

The magazine 8 also accommodates staple pushers 11 which are arranged as the staples 9 between the bottom (not shown) of the magazine 8 and the staples 9.

Each pusher 11 is shaped as a right-angle prism with a bevelled surface facing the bottom of the magazine 8. The bevelled surface has no reference number. The opposite side of the prism is flat. It faces the staples 9 and is intended to be brought into engagement with them. The flat side of the prism has no reference number. The longitudinal groove 7 receives a wedge 12 (FIG. 3) which interacts with the staple pushers 11. The wedge 12 is mounted on a carriage 13 (FIG. 1) arranged in guides 14 extending along the staple driving body 2. The guides 14 are provided on the external sides of the lateral walls of the staple driving body 2, as is shown in FIG. 1.

The mounting of the wedge 12 on the carriage 13 is described in more detail below.

The anvil body 1 has an anvil 15 which is intended to bend the ends of the staples 9 as they are brought into engagement with the anvil 15. The ends of the staples 9 have no reference number. For bending the ends of the staples 9, the anvil 15 is provided with two rows of hollows 16 spaced over the entire length of the working portion 3 of the anvil body 1. With the ligating instrument according to the invention being fully assembled, the hollows 16 are opposite the sockets of the magazine 8.

The ligating instrument of this invention further incorporates a detachable joint 17 and a locking means 18 whereby the anvil body 1 and staple driving body 2 are held together.

The detachable joint 17 is mounted on the distal ends of the working portions 3 and 5.

The detachable joint 17 comprises a stationary axle 19 and a hook 20. The axle 19 is secured on the working portion 5 of the staple driving body 2 at a perpendicular to its lateral walls.

The hook 20 is mounted on the distal end of the working portion 3 of the anvil body 1. It is intended to catch the axle 19.

The locking means 18 is located in the area where the working portions 3 and 5 extend into the handles 4 and 6, respectively. The locking means 18 is a U-shaped member. The lower part of the U member adjoins the external surface of the anvil body 1, which is opposite to its surface facing the staple driving body 2. The lower part of the U member has no reference number.

Lateral parts 21 of the locking means 18 envelop the lateral surfaces of the anvil body 1 and are fitted on a stationary axle 22 which extends through the anvil body 1 at a perpendicular to its lateral surfaces.

The lateral parts 21 have a groove receiving a stationary axle 23 which extends through the staple driving body 2 at a perpendicular to its lateral surfaces. The lateral parts 21 have flanged edges 24 (FIGS. 1 and 2) to be pressed on by the operator.

The locking means 18 further includes a lath spring 25 (FIG. 1) secured by a screw 26 screwed into the anvil body 1.

Strip-type stops 27 are provided on the lateral surfaces of the anvil body 1. The stops 27 prevent displacement of the staple driving body 2 in relation to the anvil body 1 at a perpendicular to the plane of FIG. 1.

The ligating instrument according to the invention is provided with a means 28 for adjusting the ligation spacing (FIG. 3), which is arranged in the carriage 13.

The means 28 for adjusting the ligation spacing has a stationary axle 29 mounted on the carriage 13 transversely to the latter. The tapered portion of the wedge 12 is fitted on the axle 29. The upper part of the wedge 12 is received in a recess provided in the carriage 13. The recess has no reference number.

The means 28 also incorporates a movable support 30 articulated to the wedge 12 in its rear portion. The support 30 is movable with the wedge 12 at a perpendicular to the guides 14 of the carriage 13.

A threaded through hole is provided in the body of the carriage 13. The through hole has no reference number. Its axis is perpendicular to the guides 14. The through hole accommodates a screw 31 with a nut 32. A roller 33 is fitted on the end of the nut 32 extending from the carriage 13. The roller 33 is rigidly secured to the nut 32 by a pin 34. The screw 31 has a head which serves as the movable support 30 and is designated by the same reference number. The head 30 is round in its longitudinal section, i.e., the section along the guides 14. It is accommodated in a recess provided in the rear portion of the wedge 12.

Figure 4:
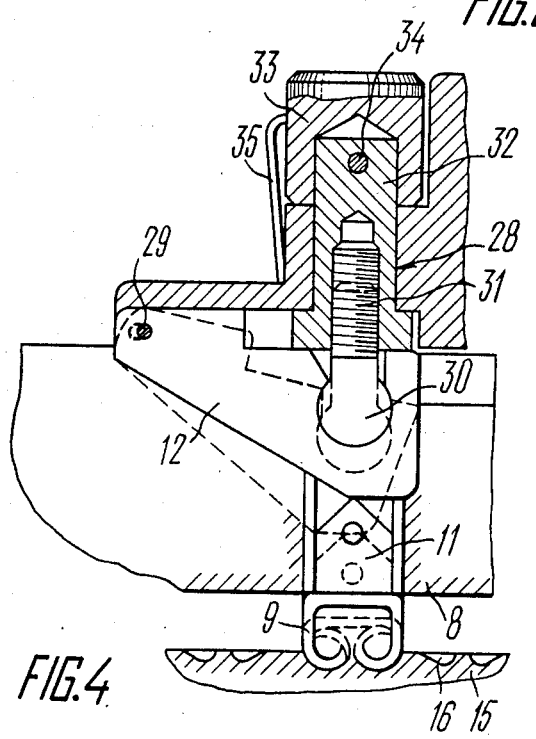
FIG. 4 is a view of the ligating instrument of FIG. 3 during ligation with the dash line showing the position of the wedge at a minimum ligation spacing.

The movable support 30 and the wedge 12 are driven transversely to the guides 14 of the carriage 13 by the screw 31 and the nut 32 as the roller 33 applies a force to the nut 32. This is clear from FIG. 4 where the dash line indicates the position of the wedge 12 with a minimum ligation spacing.

For an easy access to the nut 32, a shoulder is provided along the entire width of the carriage 13. The shoulder has no reference number.

A spring 35 is mounted on the carriage 13. It is secured in any known manner and intended to hold the roller 33 in a desired position. A scale (not shown) is provided on the lower surface of the roller 33. The reading of the scale corresponds to a given ligation spacing.

Referring to FIG. 3, the nut 32 is provided with a flange in its lower part, which is received in recesses provided in the wedge 12 and the carriage 13. The flange has no reference number.

The carriage 13 is locked in its initial position by a locking means 36 which is a cone-shaped pin with the same reference number. The pin 36 is integral with a spring 37. The tapered end of the pin 36 is received in a recess (FIG. 3) provided in the lower part of the carriage 13.

The instrument according to the present invention for ligating organs and tissues with staples operates as follows.

Before using the instrument, it is necessary to make sure that the carriage 13 is in its rearmost position, i.e., in proximity to the point where the working portions 3 and 5 of the bodies 1 and 2, respectively, are joined together. It is also necessary to ascertain that the carriage is locked in place by the locking means 36. The anvil body 1 and the staple driving body 2 must be drawn apart.

By rotating the roller 33 and using its scale, the surgeon sets a desired ligation spacing which is determined by the thickness of the tissue to be ligated. The roller 33 is locked in place by the spring 35.

The working portion 3 of the anvil body 1 is brought under the organ to be ligated, such as a stomach, and placed along the resection line. The organ is placed on the anvil 15 between the hook 20 and the stops 27.

The axle 19 mounted on the distal end of the working portion 5 of the staple driving body 2 is caught up by the hook 20, whereby the parts of the detachable joint 17 are locked together.

By using the handles 4 and 6, the surgeon brings the anvil body 1 and staple driving body 2 together, whereupon they are locked together by the locking means 18. This is done by rotating the lateral parts 21 of the locking means 18 around the stationary axle 22, after which the lateral parts 21 are brought back to their initial position by the spring 25 secured by the screw 26 to the anvil body 1.

As a result, the grooves provided on the lateral parts 21 catch the ends of the axle 23 mounted on the staple driving body 2. The carriage 13 is moved forward along the guides 14 provided on the staple driving body 2. It is moved toward the detachable joint on the distal end of the staple driving body 2 and brought to a stop, whereby it ligates the walls of the stomach with the U-shaped staples 9.

As the carriage 13 moves on, the wedge 12 is set in motion along the longitudinal groove 7 and acts on the staple pushers 11 which push the staples 9 from their sockets in the magazine 8. As the staples 9 are pushed out, their ends pierce the walls of the stomach and are brought into engagement with the hollows 16 of the anvil 15 provided on the anvil body 1, whereby they are bent, ligating the walls of the stomach.

The part of the stomach beyond the suture is cut off with a scalpel along the working surfaces of the working portions 3 and 5 of the anvil body 1 and the staple driving body 2, respectively.

The lateral parts 21 of the locking means are rotated by their flanged edges, overcoming the resistance of the spring 25. The anvil body 1 and staple driving body 2 are drawn apart by using the handles 4 and 6. The axle 19 mounted on the staple driving body 2 is disengaged from the hook 20 mounted on the anvil body 1, whereby the parts of the detachable joint 17 are disconnected.

The ligating instrument is removed from the operative wound.

Ligating instruments according to the invention have been manufactured and tested during surgical operations. The tests have corroborated all the above-mentioned advantages of the instrument according to the invention over conventional ligating instruments.

It will be apparent that by the above described invention there has been provided a simple ligating instrument which is easy to use and ensures a high quality of sutures with any ligation spacing.

What is claimed is:

1. A ligating instrument comprising an anvil body; a staple driving body; a longitudinal groove formed by the lateral walls of said staple driving body; a staple magazine with staple pushers, which is accommodated in said longitudinal groove; said anvil body having an anvil for bending the ends of the staples as they are pushed out from the magazine and brought into engagement with said anvil; a wedge intended to interact with said staple pushers of said staple magazine, received in said longitudinal groove and having a tapered portion and a rear portion; guides mounted on the external sides of the lateral walls of said staple driving body; a carriage movably mounted in said guides; said wedge being mounted on said carriage; a detachable joint; a locking means; said detachable joint and said locking means serving to hold together said anvil body and said staple driving body; a means for adjusting the ligation spacing having a stationary axle mounted on said carriage transversel to the latter, and a movable support; said wedge being fitted with its tapered portion on said stationary axle, its rear portion being articulated to said movable support; and adjusting means on said carriage for moving said wedge and said movable support transversely to said guides to adjust the ligation spacing.

2. A ligating instrument comprising an anvil body; a staple driving body; a longitudinal groove formed by the lateral walls of said staple driving body; a staple magazine with staple pushers, which is accommodated in said longitudinal groove; said anvil body having an anvil for bending the ends of the staples as they are pushed out from the magazine and brought into engagement with said anvil; a wedge intended to interact with said staple pushers of said staple magazine, received in said longitudinal groove and having a tapered portion and a rear portion; guides mounted on the external sides of the lateral walls of said staple driving body; a carriage mounted in said guides; said wedge being mounted on said carriage; a detachable joint; a locking means; said detachable joint and said locking means serving to hold together said anvil body and said staple driving body; a means for adjusting the ligation spacing having a stationary axle mounted on said carriage transversely to the latter, and a movable support; said wedge being fitted with its tapered portion on said stationary axle, its rear portion being articulated to said movable support; a means for moving said wedge and said movable support transversely to said guides of said carriage, wherein said means for adjusting the ligation spacing has a screw received in the body of said carriage, extending at a perpendicular to said guides of said carriage and having a head of a round longitudinal section, which serves as the movable support and moves with said wedge under the action of a force applied to a nut screwed on said screw.

* * * * *